United States Patent [19]
Chang

[11] Patent Number: 5,823,185
[45] Date of Patent: Oct. 20, 1998

[54] MANUAL PRESSING AND AUTOMATIC AIR BREATHING CARDIOPULMONARY RESUSCITATION FIRST-AID DEVICE

[76] Inventor: Tien-Tsai Chang, 5F, 28 Kuo-Hsiao Road, Hsin-Tien City, Taipei Hsien, Taiwan

[21] Appl. No.: 832,793

[22] Filed: Apr. 4, 1997

[51] Int. Cl.⁶ .......................... A61M 1/362; A61M 16/00; A61H 7/00; A61B 17/00
[52] U.S. Cl. .......................... 128/204.18; 600/16; 601/11; 606/201; 128/200.24; 128/205.18
[58] Field of Search .......................... 128/200.24, 204.18, 128/205.13–205.19, 206.29, 909; 600/16; 601/6–11; 606/201

[56] References Cited

U.S. PATENT DOCUMENTS

| | | | |
|---|---|---|---|
| 2,547 | 4/1842 | Welchman | 125/205.16 |
| 1,406,141 | 2/1922 | Anston | 128/205.13 |
| 2,383,181 | 8/1945 | Enslin et al. | 128/200.24 |
| 2,902,992 | 9/1959 | Renvall | 128/205.13 |
| 3,336,920 | 8/1967 | Thomas | 128/200.24 |
| 3,348,536 | 10/1967 | Tambascia | 128/200.24 |
| 3,425,409 | 2/1969 | Isaacson et al. | 128/200.24 |
| 3,509,899 | 5/1970 | Hewson | 128/204.18 |
| 3,552,390 | 1/1971 | Muller | 128/204.18 |
| 4,349,015 | 9/1982 | Alferness | 128/205.17 |
| 4,452,241 | 6/1984 | Sarnoff et al. | 128/205.13 |
| 4,870,962 | 10/1989 | Sitnik | 128/205.13 |
| 5,009,226 | 4/1991 | Holt | 128/205.18 |
| 5,109,833 | 5/1992 | Frimberger | 128/205.13 |
| 5,313,938 | 5/1994 | Garfield et al. | 128/205.16 |
| 5,327,887 | 7/1994 | Nowakowski | 128/204.18 |
| 5,657,751 | 8/1997 | Karr, Jr. | 128/205.18 |

*Primary Examiner*—Kimberly L. Asher
*Attorney, Agent, or Firm*—Ladas & Parry

[57] ABSTRACT

This invention relates to a manual pressing and automatic air breathing cardiopulmonary resuscitation first-aid device, mainly comprising a manual pressing shaft, a pump, an air storage tank, a height-adjustable stand, an air control valve and a mouth-nose breather. In operation, the manual pressing shaft is pressed to cause the pump to compress downwards such that air is compressed into the air storage tank and temporarily stored therein. Each time the manual pressing shaft is pressed downwards, the air control valve is activated to rotate a one-fifth revolution. When the manual pressing shaft is pressed five times continuously, that is, the air control valve rotates a complete revolution, the air temporarily stored within the air storage tank will be released and breathed into the patient's mouth via the mouth-nose breather. Such an action must be repeated continuously until the patient is revived.

12 Claims, 7 Drawing Sheets

MANUAL PRESSING AND AUTOMATIC AIR BREATHING CARDIOPULMONARY RESUSCITATION FIRST-AID DEVICE

BACKGROUND OF THE INVENTION

This invention relates to a manual pressing and automatic air breathing cardiopulmonary resuscitation first-aid device adapted for domestic use, the operation thereof being simple and easy. The present invention can be correctly operated without the need for special or complex practices. When a patient encounters situations such as the cessation of heart beat or respiration in a residence, even if he/she was delivered to a hospital for immediate treatment, it is still possible that his/her life may not be saved unless a person who was familiar with cardiopulmonary resuscitation (CPR) was present on site such that proper first-aid treatments could be applied. This is due to the fact that oxygen deficiency to the brain exceeding 3 to 4 minutes will result in unrecoverable damages or be life threatening. Therefore, proper treatments applied to the patient within 3 to 4 minutes during the cessation of heart beat or respiration are crucial to the survival of the patient.

For those patients suffering from high blood pressure, cardiac ailments, and respiratory system ailments, e.g. bronchitis, asthma, or pulmonary emphysema, family members must pay special attention to sudden incidents such as cessation of heart beat or respiration. When such conditions do arise, CPR must be applied to the patient immediately. The practice of CPR is substantially outlined as follows. The patient must be laid flatly on a rigid board. The clothing of the patient is then released so as to expose his chest. One person then places both hands over the notch at the intersection of the sternum and the ribs and continuously and forcefully presses five times while the other person simultaneously pinches the patient's nostrils tightly, tilts the patient's head backward; and pulls open the patient's mouth so that air can be breathed into the patient's lungs in a mouth-to-mouth manner. The patient's nostrils and mouth are then released so that the patient can breathe on his/her own. Such actions of pressing five times and then breathing once are repeated alternately until the patient is revived. If only one person is present on site, pressing must be applied to the patient continuously for 15 times and then air is breathed into the patient twice until the patient is revived.

However, breathing air in a mouth-to-mouth manner can easily cause contact infection. Though there already exists a mask-type device which utilizes the check-valve principle to impede air from reversibly flowing toward the mouth of the rescuer so as to prevent one-way infection, the possibility of two-way infection still cannot be eliminated during air breathing. Furthermore, CPR requires professional training in order to attain its intended effects. In view of the above situations, it is necessary to provide a device that can be efficiently and correctly applied by the family members during the sudden incidents with simple and easy operations.

BRIEF DESCRIPTION OF THE INVENTION

A semi-mechanical manual pressing and automatic air breathing cardiopulmonary resuscitation first-aid device is provided in view of the foregoing needs. Since the operation thereof is simple and easy, the general public can apply first-aid treatments to the patient without help from medical personnel.

An advantage of the present first-aid device resides in that the rescuer avoids direct contact with the patient so as to prevent any disease infection. The components that are in direct contact with the patient's mouth and nose can be dismantled for disposal and replacement after each use to thereby prevent infecting the next patient to which the device is applied.

Aside from the foregoing benefits, the most important feature resides in that air is breathed into the patient's lungs once every five times the patient's chest is pressed so that the two actions collaborate effectively, alternately, and continuously, to thereby facilitate the rapid revival of the patient. Such feature is unlike the conventional first-aid method, which involves the actions of pulling open the patient's mouth, tightly pinching the patient's nose, and breathing into the patient's lungs once every five times the cardiopulmonary area is being pressed, and where such actions can be accommodated continuously only with difficulty, resulting in the missing of critical rescuing moments. In addition, the first-aid device further can be provided with an oxygen-supplying valve for providing sufficient oxygen to the patient's brain so as to increase the patient's survival rate and to avoid complications, such as hemiplegia or brain death, that may result from the conventional first-aid method.

Another benefit of using the present first-aid device is that the rescuer's stamina is conserved. When applying CPR, not only must the patient's chest be pressed forcefully, but air must also be breathed into the patient's lungs forcefully. Such repetitive actions will tend to completely exhaust the rescuer. Not everyone is capable of managing such a first-aid method.

Because the present first-aid device consists of an automatic air-breathing function, it minimizes depletion of the rescuer's stamina. In summary of the above benefits, using the present first-aid device allows the general public to manage rescuing a person only with simple practice.

DETAILED DESCRIPTION OF THE PREFERRED EMBODIMENT

The structural principles and operational procedures of the preferred embodiment of the present invention are expounded as follows with reference to the figures of the accompanying drawings. (1) Structure and Principle Reference is first made to FIGS. 1 and 2, wherein the present invention substantially comprises a manual pressing shaft 1, a pump 2, an air storage tank 3, a frame 4, a height-adjustable stand 5, an air control valve 6, a sucking disk 7, a mouth-nose breather 8, and an air passage pipe 9.

Figure 1:
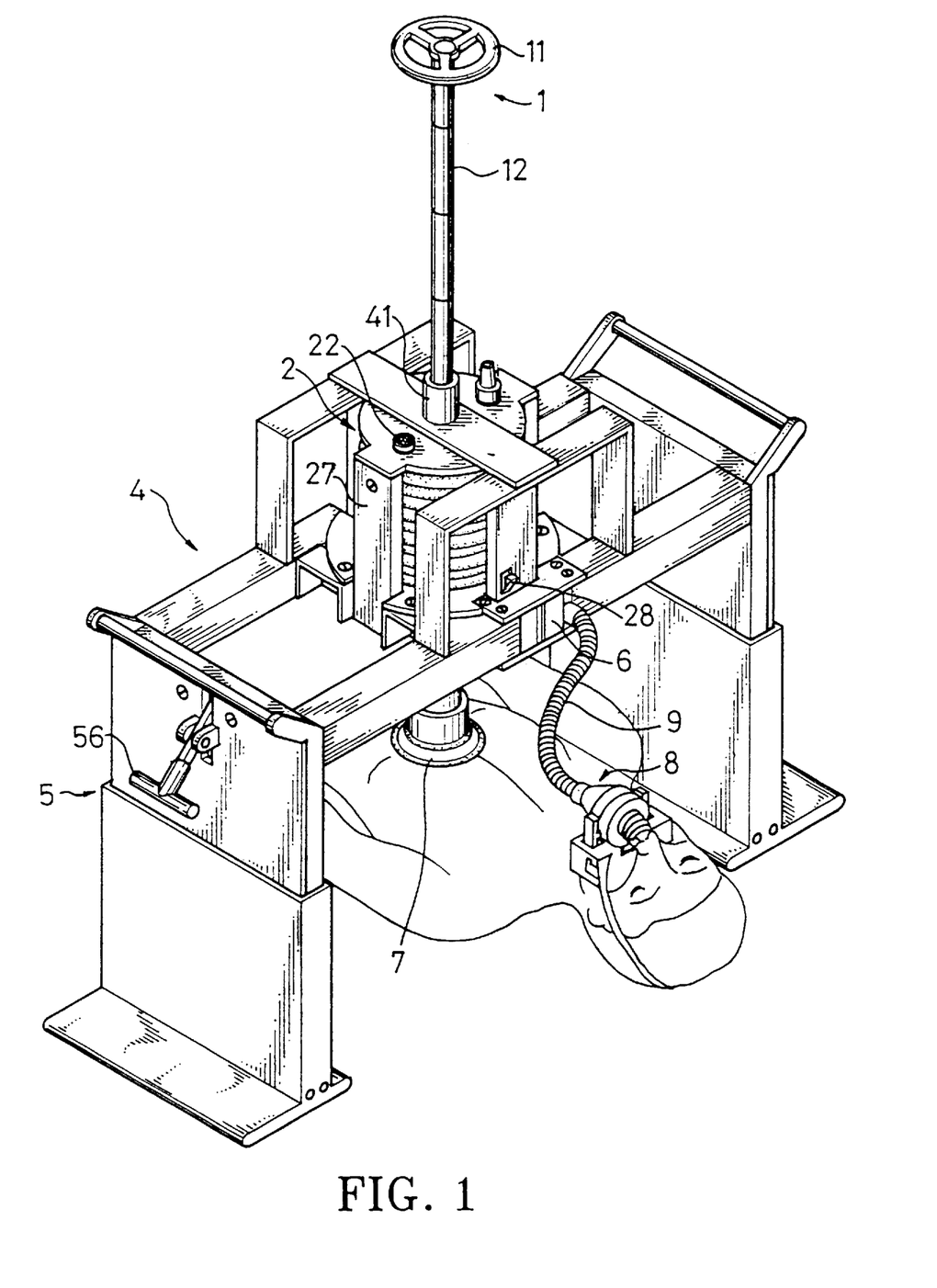
FIG. 1 illustrates a schematic view of the appearance of the present invention.
Figure 2:
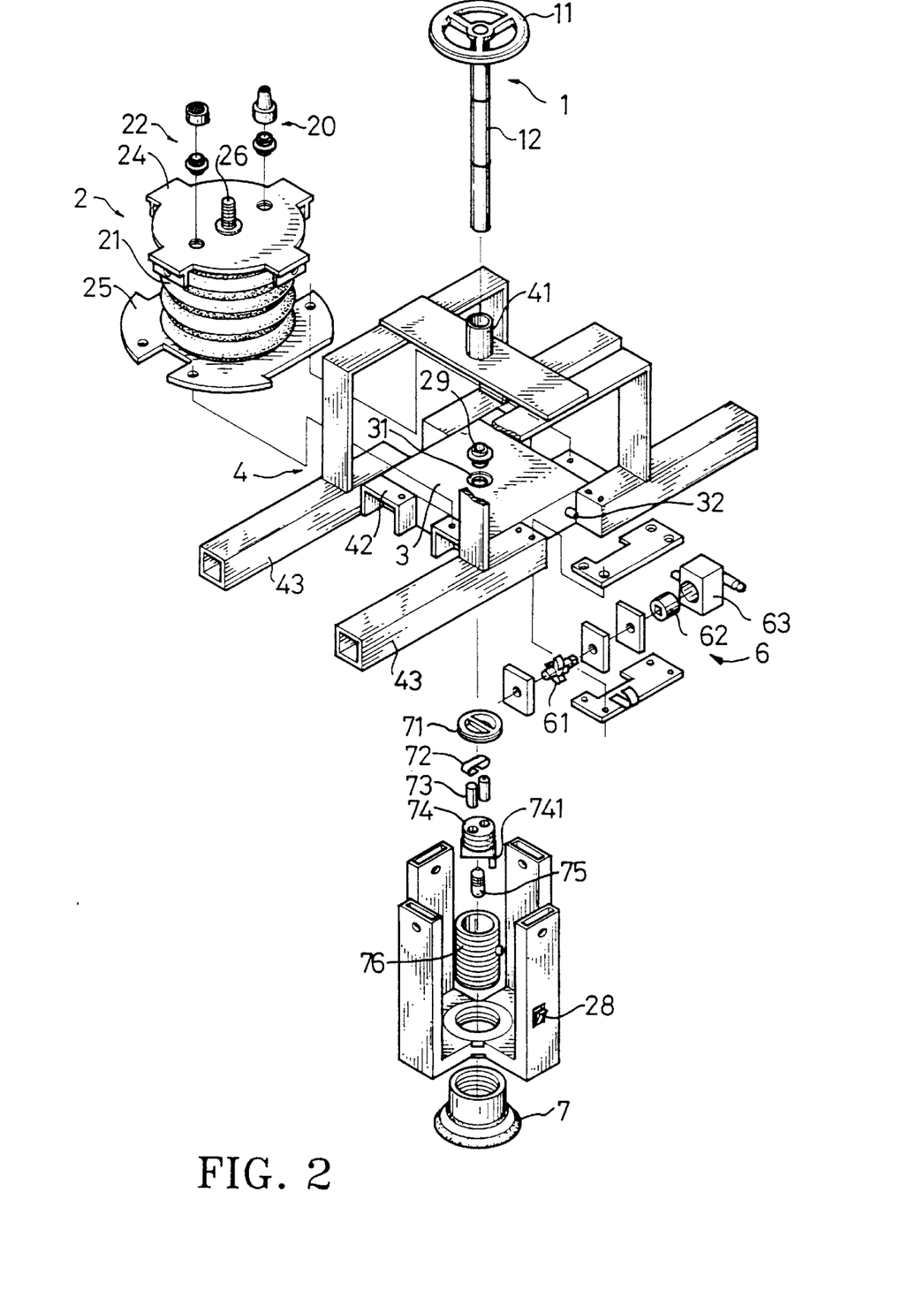
FIG. 2 illustrates an exploded view of the manual pressing shaft, the pump, the air control valve and the sucking disk of the present invention.

The manual pressing shaft 1 is provided with a circular handle 11 and an elongated shaft body 12, wherein the shaft body 12 can be of a multi-sectional type and the assembled length thereof is governed by the most convenient pose of the rescuer and can be predetermined. The manual pressing shaft 1 passes through a circular hole 41 formed on the frame 4 and the end thereof is affixed to a screw 26 at the center of the pump 2.

The pump 2 includes a retractable air sack 21, the top and bottom of which includes an upper cover 24 and a bottom cover 25, respectively. The bottom of the upper cover 24 is connected to a supporting rack 27 and a one-way valve 22 only permitting air to enter the air sack 21 from outside is provided thereon. The upper cover 24 further can be provided with a one-way valve 20 thereon for connecting to an oxygen source (not shown). When the oxygen source is unavailable, a cap can be used to seal the one-way valve 20. The bottom cover 25 is affixed onto the frame 4 and is connected to the air-storage tank 3 via a one-way valve 29 so that air is compressed therein from the inside of air sack 21. As shown in the embodiment, the pump 2 includes a retractable air sack having a bellows shape.

Figure 3A:
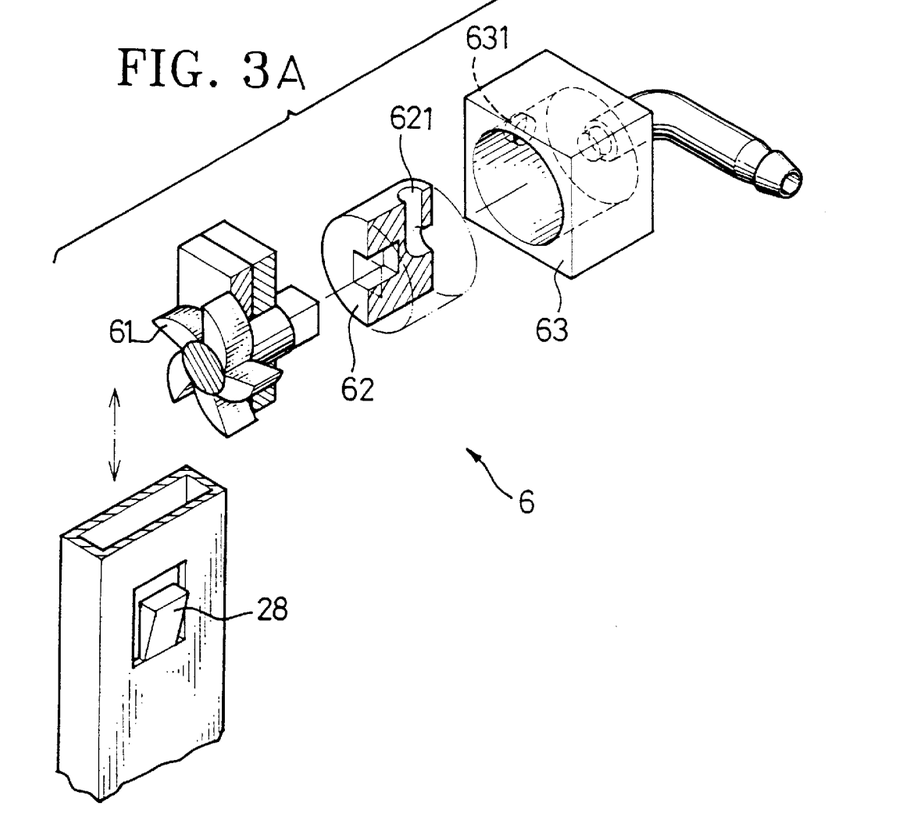
FIG. 3A illustrates an exploded view of the air control valve of the present invention.
Figure 3B:
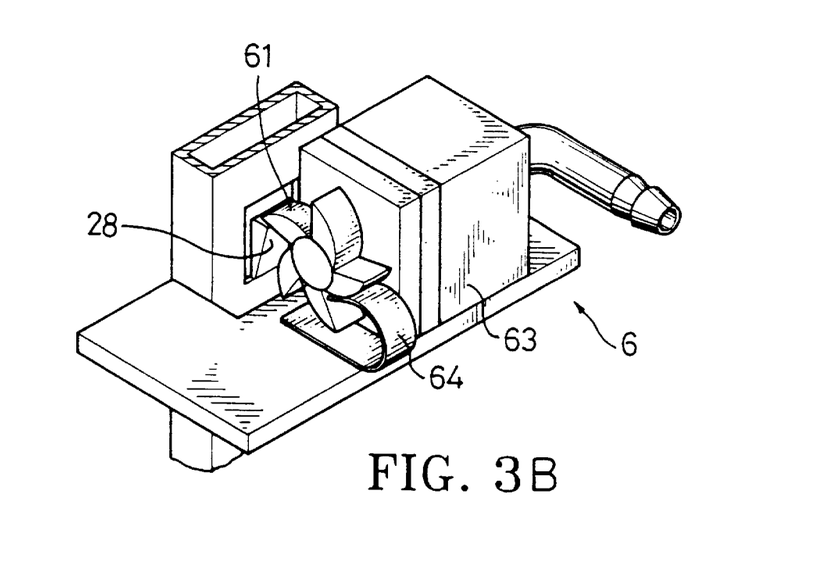
FIG. 3B illustrates an assembled view of the air control valve of the present invention.

The frame 4 which provides the primary supporting structure of the present first-aid device includes two main trusses 43, a mounting base 42 and a circular hole 41 formed thereon. The manual pressing shaft is inserted therein through the circular hole 41. The circular hole 41 also facilitates a stable action while pulling and pushing the manual pressing shaft. The air storage tank 3 is mounted on the mounting base 42. The air storage tank 3 provides an enclosure having an appropriate volume and an opening 31 is formed thereon for connecting to the bottom cover 25 via the one-way valve 29. A hole 32 is further formed on the side of air storage tank 3 in communication with the air control valve 6. The air control valve 6 includes a gear 61, a cylindrical core shaft 62 and a hollow valve body 63. With reference to FIGS. 1, 3A, and 3B, when the manual pressing shaft 1 is pressed downwards, the supporting rack 27 also moves downwards. A clip 28 is provided on the supporting rack 27 such that the clip 28 contacts the teeth of gear 61 when the supporting rack 27 moves downwards and that the gear 61 is urged against a clinching plate 64 to avoid further revolution thereby forcing the clip 28 to retract inwards. When the manual pressing shaft is pulled upwards, the clinching plate 64 is no longer clinched onto the gear 61 and the clip 28 will force the gear 61 to rotate for an angle. The gear 61 preferably includes five teeth such that an angle of 72° is rotated each time. Hence, every five times the manual pressing shaft 1 is pulled upwards, the gear 61 rotates one complete revolution. The center of gear 61 is connected to one end of the core shaft 62. A passageway 621 is formed within the core shaft 62 from the side of core shaft 62 and penetrates through one end thereof. The core shaft 62 is rotatably fitted within the cylindrical hole 632 of the valve body 63. A first small hole 631 is formed on the side of valve body 63, and a second small hole 633 is formed at the rear wall thereof. When the side inlet of passageway 621 of the core shaft 62 is aligned with the location of the first small hole 631 of valve body 63, the air inside the air storage tank 3 flows outwards through the air control valve 6. However, after the next upward-pulling action of the manual pressing shaft 1, the core shaft 62 rotates for an angle and the passageway 621 is thus sealed until the upward-pulling action is conducted five times such that the core shaft 62 rotates a complete revolution to return to the initial state and the passageway 621 is thus re-opened.

Figure 4:
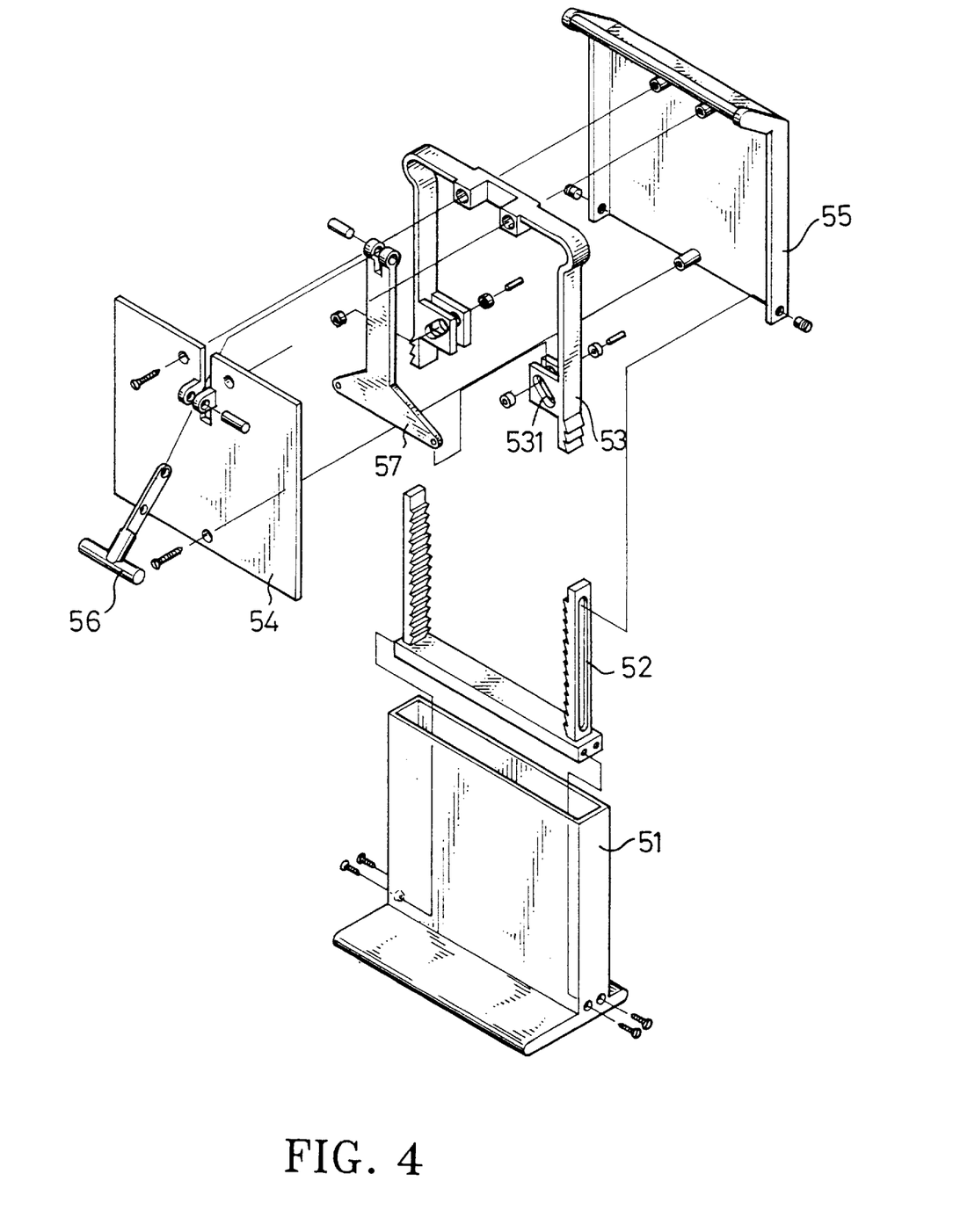
FIG. 4 illustrates an exploded view of the base portion of the present invention.
Figure 5:
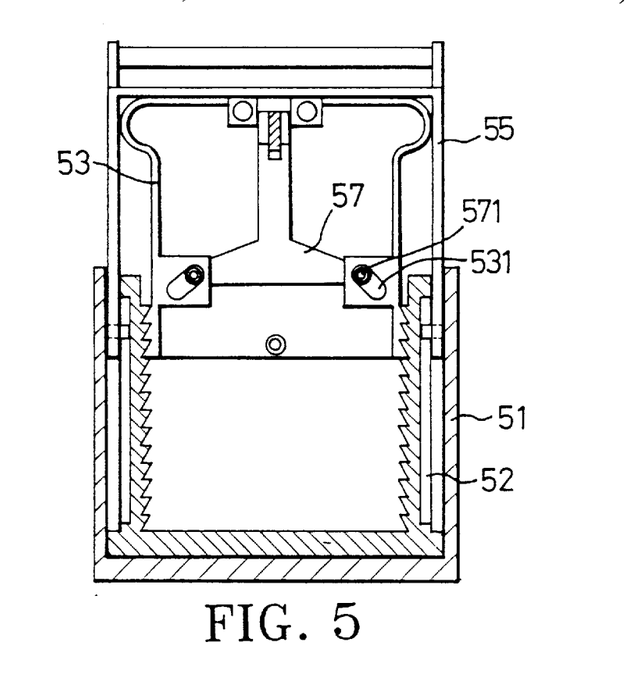
FIG. 5 is an assembled view of the base portion illustrated in FIG. 4, illustrating the state in which the inverse U-shaped rail of teeth is engaged with the parallel rails of teeth.
Figure 6:
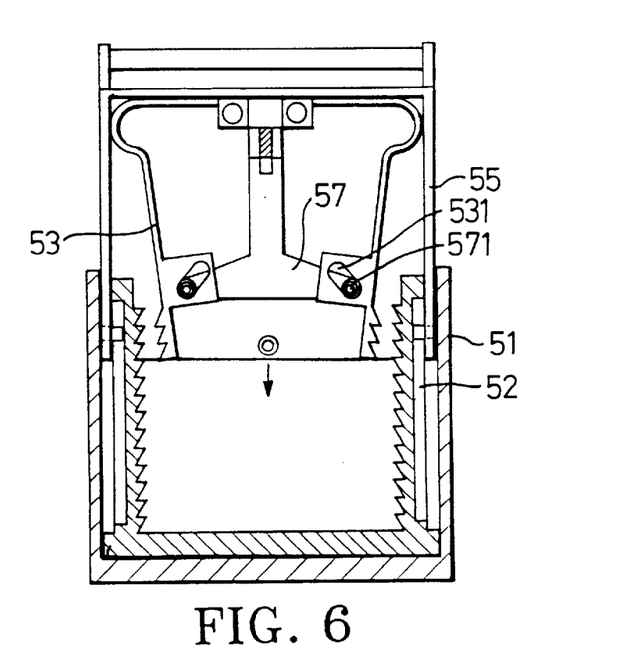
FIG. 6 is an assembled view of the base portion illustrated in FIG. 4, illustrating the state in which the inverse U-shaped rail of teeth is disengaged from the parallel rails of teeth.

With reference to FIGS. 1 and 4, a set of height-adjustable stands 5 is provided at the opposite sides of the frame 4. The stands 5 include a hollow base 51, in which a pair of parallel rails of teeth 52 is mounted to form a mounting portion, and a flat board is extended outwardly from each of the opposite locations where the stands 5 contact the ground as a stepping board for the rescuer. A further inverse U-shaped rail of teeth 53 is adapted to be interengaged with the parallel rails of teeth 52 by means of the ratchets thereof. The U-shaped rail of teeth covered by an external cover 54 and an internal cover 55 cooperate to form a mobile portion. With reference to FIGS. 5 and 6, two elongated and oblique slots 531 are each formed on the opposite sides of the open end of the inverse U-shaped rail of teeth 53. The U-shaped rail of teeth 53 is activated to retract and to expand by means of a height-adjusting control shaft 56 and an inverse T-shaped coupling shaft 57, wherein the principle resides in that a roller 571 is provided at each of opposite ends of the inverse T-shaped coupling shaft 57 such that the rollers 571 are rolled within the elongated and oblique slots 531 of the inverse U-shaped rail of teeth 53. When the height-adjusting control shaft 56 is pulled up, the inverse T-shaped coupling shaft 57 moves downwards such that the rollers 571 move downwards so as to force the inverse U-shaped rail of teeth 53 to retract and to cause the ratchets to disengage from the parallel rails of teeth 52 whereby the entire mobile portion freely moves up-and-down so as to adjust the height thereof, as shown in FIG. 6. The height-adjusting control shaft 56 is released after an appropriate height has been attained. The inverse U-shaped rail of teeth 53 is made of recoverable and resilient substance such that the open end of the U shape expands and inter-engages with the ratchets of the parallel rails of teeth 52 so as to be affixed thereto, as shown in FIG. 5.

As shown in FIG. 2, the sucking disk 7 is affixed beneath the supporting rack 27 so as to follow the manual pressing shaft 1 to move up and down. During the first-aid operation, the sucking disk 7 is urged flatly against the notch portion at the intersection of the patient's exposed sternum and ribs, as shown in FIG. 1. When the manual pressing shaft 1 is forcefully pressed downwards, the sucking disk 7 adheres to the notch portion due to the pressure.

When the manual pressing shaft 1 is pressed downwards from the top, not only does the air fill the air storage tank 3 via the pump 2, the clip 28 activating the gear 61 to drive the core shaft 62 of the air control valve 6 to rotate, but the sucking disk 7 is also pushed downwards (for 4 to 5 cm preferably) deeply reaching the cardiopulmonary area, thereby forcing the blood within the heart to be transported to the capillaries of the entire body via the circulating artery. When the sucking disk 7 is pressed to a fixed location, the rescuer pulls the handle 11 upwards from the bottom, the skin to which the sucking disk 7 is adhered is thus pulled outwards and bulges in response thereto, such that the pressure applied to the patient's heart is released suddenly and the flow rate from the vein and the pulmonary vein to the heart is increased.

Figure 7:
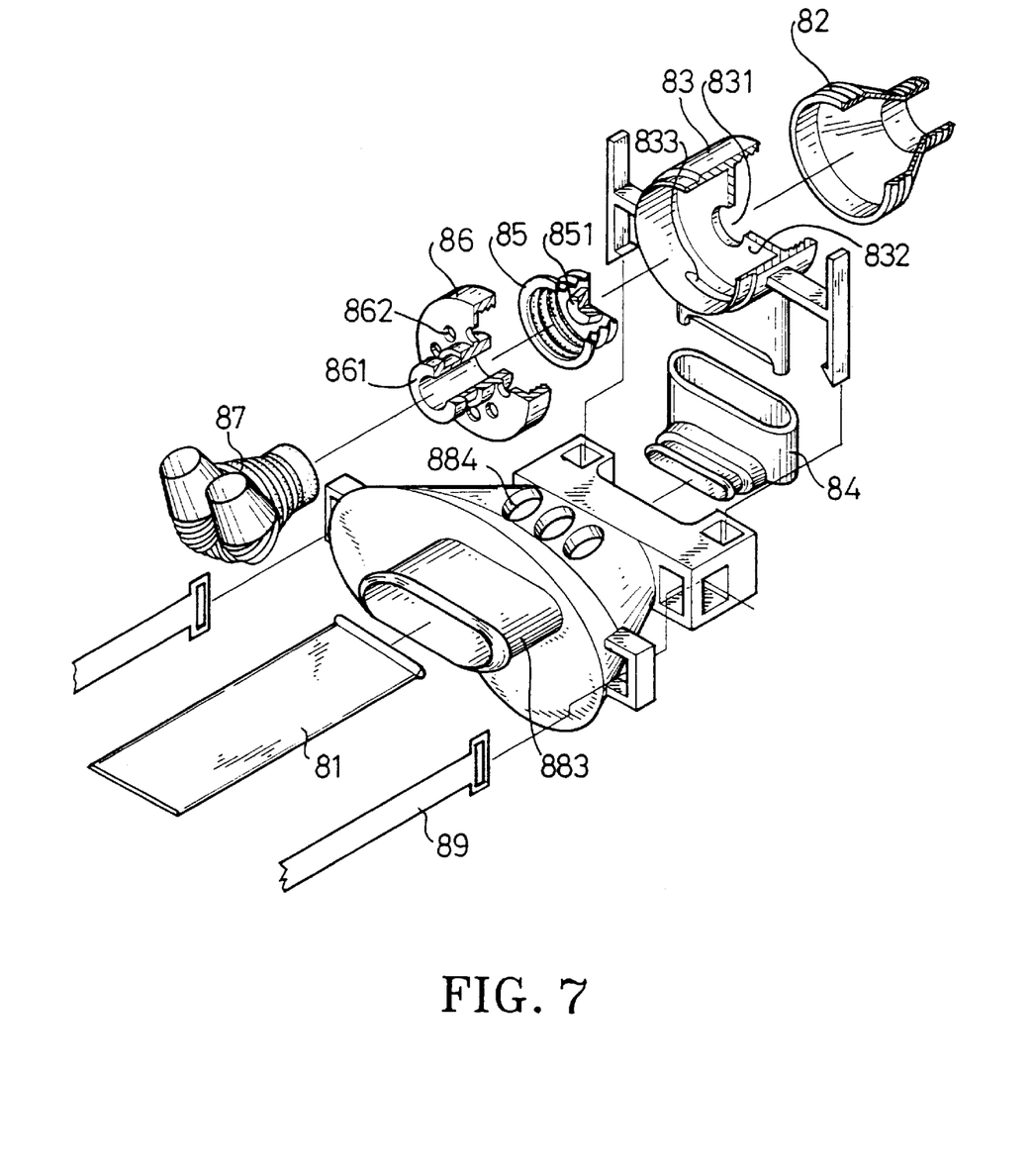
FIG. 7 illustrates an exploded view of the mouth-nose breather of the present invention.
Figure 8:
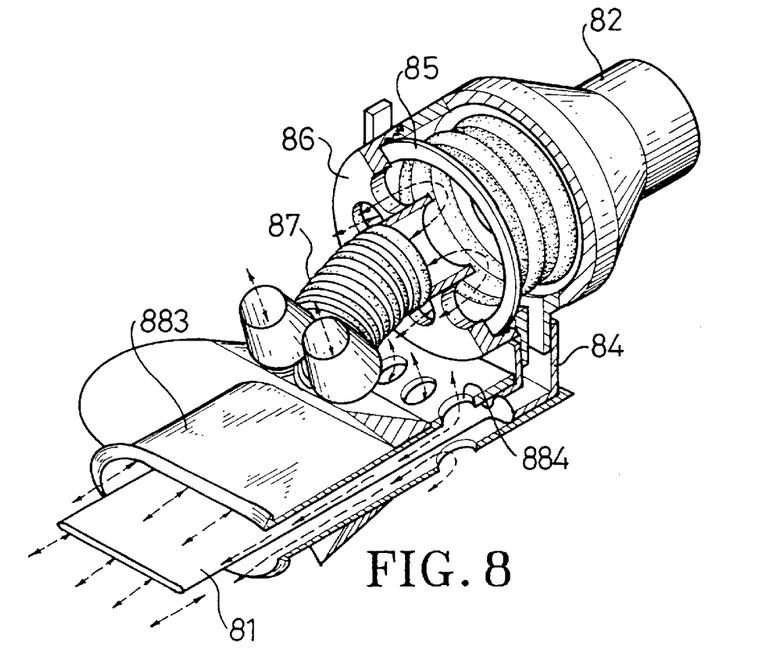
FIG. 8 shows the mouth-nose breather illustrated in FIG. 7, illustrating the schematic view of the patient's mouth and nose breathing freely through the non-inflated gap and the small holes of the mouth-holder and the hose as well as the air passage pipe in communication with both nostrils.
Figure 9:
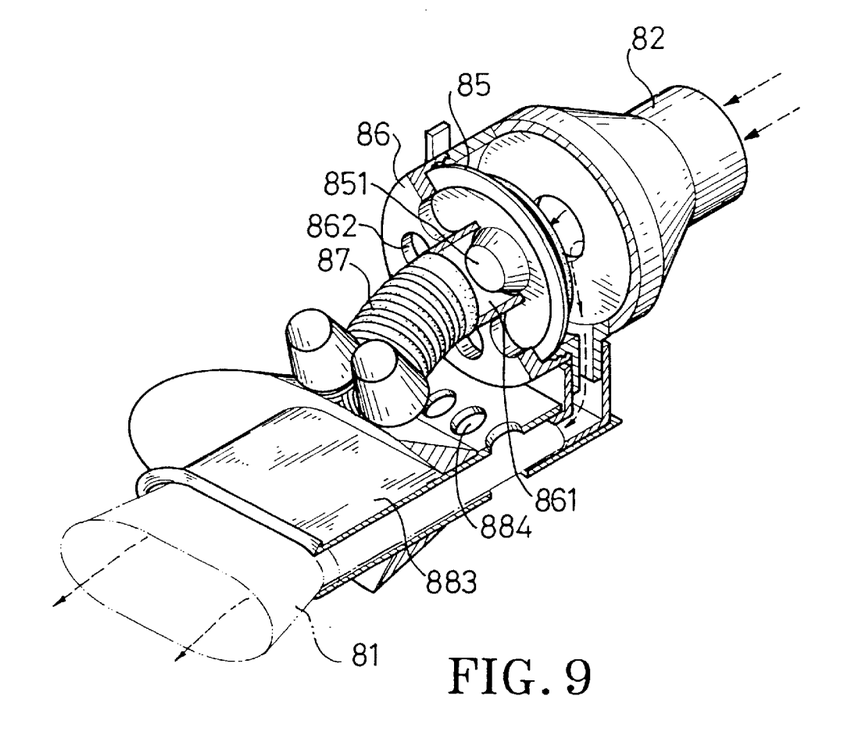
FIG. 9 shows the mouth-nose breather illustrated in FIG. 7, illustrating the schematic view of the "two-way valve" blocking the nose and respiratory tract, which replaces the action of pinching the patient's nostrils, and the hose being inflated within the mouth-holder for blocking the mouth and respiratory tract.

As illustrated in FIG. 1, the mouth-nose breather 8 is connected to the air control valve 6 via an air passage pipe 9. The air stored in the air storage tank 3 is breathed into the patent's lungs via the mouth-nose breather 8 and the detailed structure of the mouth-nose breather 8 is illustrated in FIG. 7. When the air control valve 6 is open, high pressure air flows from the air storage tank 3 and passes the air passage pipe 9 and a coupling sleeve 82 to directly reach the air-turning baffler 83 thereby pushing the two-way valve 85 initially blocking a central air passage hole 831 formed on a central baffle 832 of the air duct to move forward. A frusta-conical cylinder 851 of the two-way valve 85 adapts to block the internal tube of an air passage tube 861 of the nostril breather 86 (as shown in FIG. 9) such that the patient is temporarily unable to breathe through the nostrils, which effect is equivalent to the action of manually pinching the nostrils. At the same time, the air which has already entered the air passage hole 831, having no other passageway, pushes open the two-way valve 85 to enter a hose 81 disposed within a mouth holder 883 from a turning hole 833 via a sleeve 84, the sleeve having two ends and being hollow inside. The air rapidly inflates the hose 81 so as to fill the inside of the entire mouth holder 883 and to completely seal the mouth holder 883 and mouth breathing holes 884 simultaneously. A hollow mask 88 is adapted to the shape of mouth for deterring the mouth holder 883 or the hose 81 from sinking deeply into the patent's mouth. The mouth holder 883 is made of a rigid substance and has one end adapted to be inserted into the mouth of the patient, and another end connected with one end of the sleeve 84. At this time, the air will enter the patient's lungs. This method replaces the action of breathing air into the patient's mouth in a mouth-to-mouth manner adopted by the current first-aid resuscitation method. When the rescuer activates the handle 11 to move up and down using both hands, the gear 61 rotates the core shaft 62 for an angle such that the first small hole 631 and passageway 621 slip by each other to prevent air from passing through so that no air flows within the air duct 9 and the turning air baffler 83. Therefore, the two-way valve 85 that was moved forward by air and blocked the inside of the air passage tube 861 of the nostril breather 86 rebounds to the initial state, and opens the baffle 832. At this time, air inside the patient's lungs is dissipated freely through the nostrils, the nostril three-way pipe 87, the air passage tube 861 provided on the nostril breather 86 and nose breathing holes 862. The nostril three-way pipe 87 is formed with two holes at one end thereof for connecting with the nose of the patient, and is formed with a hole at the other end thereof for connecting with the air passage tube 861. The hose 81, disposed inside the mouth holder 883, retracts back to the original shape in the absence of air therein so as to increase the gap between the tube opening of the mouth holder 883 and the hose 81. Therefore, when air is not breathed into the patient, air inside the patient's lungs is exhaled from the mouth, the increased gap, and the breathing holes 884.

Furthermore, an indicating light bulb set can be provided on the sucking disk 7. The indicating bulb set is composed of a battery cover 71, an electrode plate 72, batteries 73, a battery box 74, an electrical conductive plate 741, a bulb 75, a bulb set housing 76 and a switch 761. When the switch 761 is pressed, the electrical conductive plate 741 contacts the light bulb 75 to light the bulb. The light projecting from the indicating bulb helps the operator to direct sucking disk 7 to the pressing location of the patient's chest.

(2) Process of operation

During the first-aid operation, the patient is quickly laid flatly on a rigid board. The clothing of the patient is then released so as to expose his chest. The preparation is identical to that of conventional CPR and will not be described here again. The present first-aid device is then properly installed. In preparation, the present first-aid device should be straddled over the patient's chest such that the sucking disk 7 is aimed at the notch portion at the intersection of the patient's sternum and ribs. Or, the switch 761 is pressed to light the light bulb 75 such that the operator can easily aim the sucking disk 7 at the aforementioned notch portion of the patient which is located via the projecting light. The height-adjusting shaft 56 is then pulled up to adjust the stands 5 such that the sucking disk 7 adapts to contact the notch portion. The control shaft is then released to fix its height.

The nostril three-way pipe 87 and the mouth-holder 883 are then inserted into the patient's nostrils and mouth, respectively, with proper adjustment, and affixed to the patient's head by a Velcro® belt 89 (as shown in FIG. 1).

The rescuer then tightly grasps the handle 11 and pushes downwards. The manual pressing shaft 1 and the upper cover 24 of the pump 2 are pressed downwards simultaneously causing the pressure inside the pump 2 to increase, thereby shutting the one-way valve provided on the pump and opening the one-way valve in communication with the air storage tank at the same time, such that the air inside the pump 2 completely enters the air storage tank via the one-way valve. The handle is then pulled upwards such that the upper cover 24 of the pump 2 connected to the manual pressing shaft 1 is raised in response thereto. At this moment, the pump 2, which is close to a vacuum, suddenly shuts off the one-way valve connecting to the air storage tank 3 in order to prevent the air which has already entered the air storage tank from flowing in a reverse direction, and to open the one-way valve simultaneously so as to fill the inside of pump 2 with air. The action of pushing and pulling the manual pressing shaft is repeated until the patient is revived.

The foregoing explanation is directed to the description of the preferred embodiment according to the present invention. Various changes and implementations can be made by those skilled in the art without departing from the technical concept of the present invention. Since the present invention is not limited to the specific details described in connection with the preferred embodiment except for those that may be within the scope of the appended claims, changes to certain features of the preferred embodiment without altering the overall basic function of the invention are contemplated.

What is claimed is:

1. A manual pressing and automatic air breathing cardiopulmonary resuscitation first-aid device, comprising:

a manual pressing shaft having a handle and a straight shaft body that moves up and down;

a pump to be activated by said manual pressing shaft and having a variable internal enclosure for compressing air;

an air storage tank in communication with the pump for temporarily storing air compressed therein by said pump;

a sucking disk disposed beneath said air storage tank and moving up and down in response to said manual pressing shaft so as to be pressed against the patient's chest receptively;

a pair of stands connected to opposite sides of said air storage tank to be straddled over the patient;

an air control valve in communication with said air storage tank comprising an air valve, which is open once for a fixed number of times that the manual pressing shaft moves up and down;

a mouth-nose breather for covering the patient's mouth and nose, and being in communication with said air storage tank through said air control valve mechanism by means of an air duct, wherein said mouth-nose breather simultaneously opens the patient's mouth passageway and shuts the patient's nose passageway when said air control valve is open, and air inside said air storage tank is uni-directionally guided into the patient's mouth, and wherein the patient's nose passageway is open causing the air previously guided into the patient's mouth and entering the lungs to be guided out from the mouth and nose when said air valve is shut off.

2. A manual pressing and automatic air breathing cardiopulmonary resuscitation first-aid device according to claim 1, wherein said shaft body of said manual pressing shaft is multi-sectional so as to be assembled or adjusted into a proper length thereby being adapted to various rescuers.

3. A manual pressing and automatic air breathing cardiopulmonary resuscitation first-aid device according to claim 1, wherein said pump is a retractable air sack having a variable enclosure and has a bellows shape.

4. A manual pressing and automatic air breathing cardiopulmonary resuscitation first-aid device according to claim 1, wherein said pump includes an upper cover for assembling onto said manual pressing shaft so as to activate said upper cover to compress air while pulling or pushing forcefully, and a lower cover for affixation to said air storage tank, a hole being formed on each of said upper and lower covers, and each hole is tightly connected to a one-way valve such that air inside said pump is guided into said air storage tank through said one-way valve provided on said lower cover when said upper cover of said pump is pressed downwards, and that air outside said pump is guided into said pump through said one-way valve provided on said upper cover when said upper cover of said pump expands upward.

5. A manual pressing and automatic air breathing cardiopulmonary resuscitation first-aid device according to claim 4, wherein said upper cover is further provided with another one-way valve for connecting to an oxygen source.

6. A manual pressing and automatic air breathing cardiopulmonary resuscitation first-aid device according to claim 1, wherein said air storage tank is formed with a hollow enclosure and has an inlet and an outlet.

7. A manual pressing and automatic air breathing cardiopulmonary resuscitation first-aid device according to claim 1, wherein said stands are retractable for adjusting the height of said sucking disk.

8. A manual pressing and automatic air breathing cardiopulmonary resuscitation first-aid device according to claim 7, wherein a flat board is extended outwardly from each of the opposite locations where said stands are in contact with the ground as a stepping board for the rescuer.

9. A manual pressing and automatic air breathing cardiopulmonary resuscitation first-aid device according to claim 7, wherein the stands comprise a pair of parallel rails of teeth and an inverse U-shaped rail of teeth; said inverse U-shaped rail of teeth is provided with height-adjusting control shaft, wherein ratchets and teeth are inter-engaged under normal circumstances; and said height-adjusting control shaft is pulled such that two free ends of said inverse U-shaped rail of teeth retracts inwards causing said ratchets to disengage from said teeth and the height is freely adjusted when desired.

10. A manual pressing and automatic air breathing cardiopulmonary resuscitation first-aid device according to claim 1, wherein said pump is provided with a supporting rack for connecting to said upper cover of said pump, and supporting rack being further provided with a clip mechanism for resiliently retracting inwards; said air control valve comprises:

a gear, preferably having five teeth with equally distributed angles;

a clinching plate for clinching to said gear and preventing said gear from rotating in a reverse direction;

a valve body, one side of which being formed with a cylindrical hole without penetrating through said body, the other side of which being formed with a first small hole in communication with said cylindrical hole, and a second small hole being formed on the wall of said cylindrical hole and penetrating such wall and in communication with said outlet of said air storage tank; and an air control valve core shaft shaped in a cylinder being connected to said gear and adapted to said cylindrical hole of said air control valve body so as to be freely rotatable within said cylindrical hole, said core shaft being formed with an air passageway being in communication with said first and second small holes respectively formed on said wall of said cylindrical hole and said valve body, whereby said gear is rotated for one-fifth revolution every time said manual pressing shaft is pressed downwards and said gear is rotated for a complete revolution every five times said manual pressing shaft is pressed downwards such that air is allowed to flow through said air passageway formed on said air control valve once.

11. A manual pressing and automatic air breathing cardiopulmonary resuscitation first-aid device according to claim 1, wherein said mouth-nose breather comprises:

an air duct being a flexible hollow tube, one end of which being connected to said air control valve;

an air turning baffler connecting to another end of said air duct;

a two-way valve having a substantially cylindrical shape, located within said air turning baffler and made of resilient substance, one end of such two-way valve is further provided with a projection shaped like a cone or a frusta-cone;

a nostril breather having an air passage tube in the center thereof, and formed with a plurality of holes at the periphery thereof; one end of said air passage tube faces said two-way switch valve;

a nostril three-way pipe, one side of which is formed with two holes for connecting with the nose, the other side of which is formed with a hole for connecting with the other end of air passage tube of said nostril breather;

a sleeve having two ends and being hollow inside, and with one end of which connecting with said air turning baffler;

a mouth holder made of rigid substance, having one end adapted to be inserted into the mouth of the patient, and having the other end connected with the other end of said sleeve;

a hose entirely penetrating said mouth holder, one end of which being coupled to said mouth holder to be held inside the patient's mouth, another end of which being connected to said air turning baffler; and a hollow mask adapted to the shape of the mouth for deterring said mouth holder or said hose from sinking deeply into the patent's mouth.

12. A manual pressing and automatic air breathing cardiopulmonary resuscitation first-aid device according to claim 1, wherein said sucking disk is provided with an indicating light bulb set comprising a battery cover, an electrode plat, batteries, a battery box, an electrical conductive plate, a light bulb, a bulb set housing and a switch and wherein, when the switch is pressed, said electrical conductive plate contacts said light bulb to light the bulb so as to facilitate said sucking disk to aim at the pressing location of the patient's chest via the projection of said bulb.

* * * * *